United States Patent [19]

Lancellotti

[11] 4,191,373
[45] Mar. 4, 1980

[54] TENNIS ELBOW BRACE

[76] Inventor: William E. Lancellotti, 371 Broadway, Providence, R.I. 02903

[21] Appl. No.: 748,111

[22] Filed: Dec. 6, 1976

[51] Int. Cl.² ............................................. A63B 69/38
[52] U.S. Cl. .................................. 273/29 A; 128/77; 128/88
[58] Field of Search .............. 273/29 R, 29 A, 189 R, 273/189 A; 128/77, 80 R, 80 B, 80 C, 80 E, 80 F, 87 R, 88, 165; 2/16, 22, 209; 3/12, 12.2, 12.3, 1.91, 22; 403/110

[56] References Cited

U.S. PATENT DOCUMENTS

| | | | |
|---|---|---|---|
| 522,143 | 12/1895 | Rankin | 128/88 |
| 1,226,160 | 5/1917 | Allis | 273/189 A |
| 1,466,487 | 8/1923 | Shaffer | 128/88 |
| 1,622,211 | 3/1927 | Sheehan | 128/80 C |
| 2,467,907 | 4/1949 | Peckham | 128/88 |
| 3,505,684 | 4/1970 | Hutchinson et al. | 2/209 |
| 3,506,981 | 4/1970 | Stewart et al. | 2/209 |
| 3,814,419 | 6/1974 | Bjorklund | 273/29 A X |
| 3,884,240 | 5/1975 | Gilman | 2/209 |

FOREIGN PATENT DOCUMENTS 295632 12/1916 Fed. Rep. of Germany .......... 128/80 B
125511 4/1919 United Kingdom ...................... 128/88

OTHER PUBLICATIONS

Journal of Bone and Joint, vol. XXIII, #3, pp. 712, 713 by William Tobin, Jul. 1941.

Primary Examiner—Richard C. Pinkham
Assistant Examiner—T. Brown
Attorney, Agent, or Firm—Salter & Michaelson

[57] ABSTRACT

A brace adapted for wear by a tennis player for minimizing and/or preventing tennis elbow comprising in its most basic form a pair of discs adapted for respective generally nonslip compressive contact with that portion of the player's arm directly overlying the medial and lateral eipcondyles thereof. The discs are generally of cup-shaped internal configuration having a somewhat compressible surface for engaging the player's skin. Bracket means enable the mounting of such discs in spaced opposition from each other and permit their independent rotation so as to follow the movements of the player's arm.

14 Claims, 25 Drawing Figures

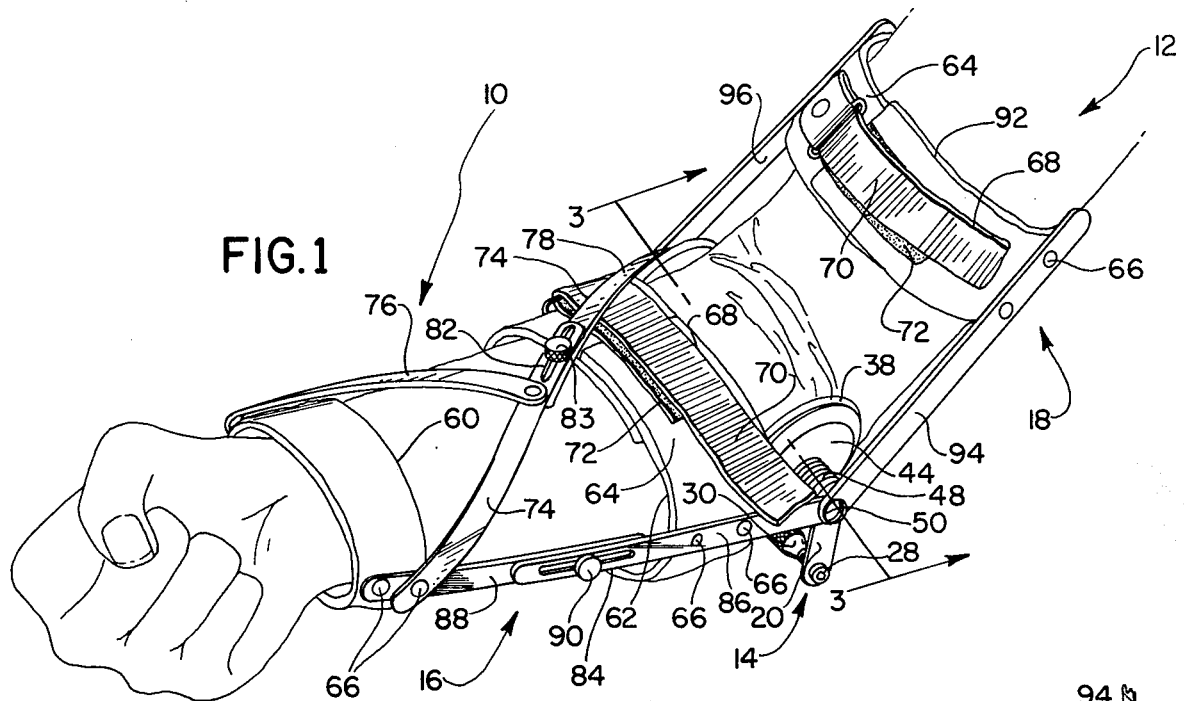
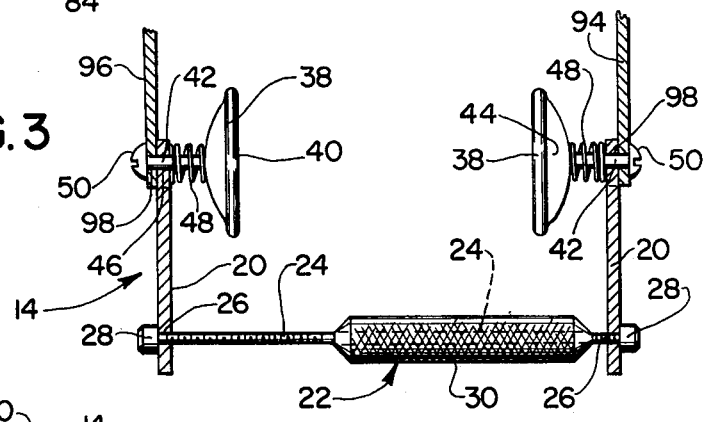
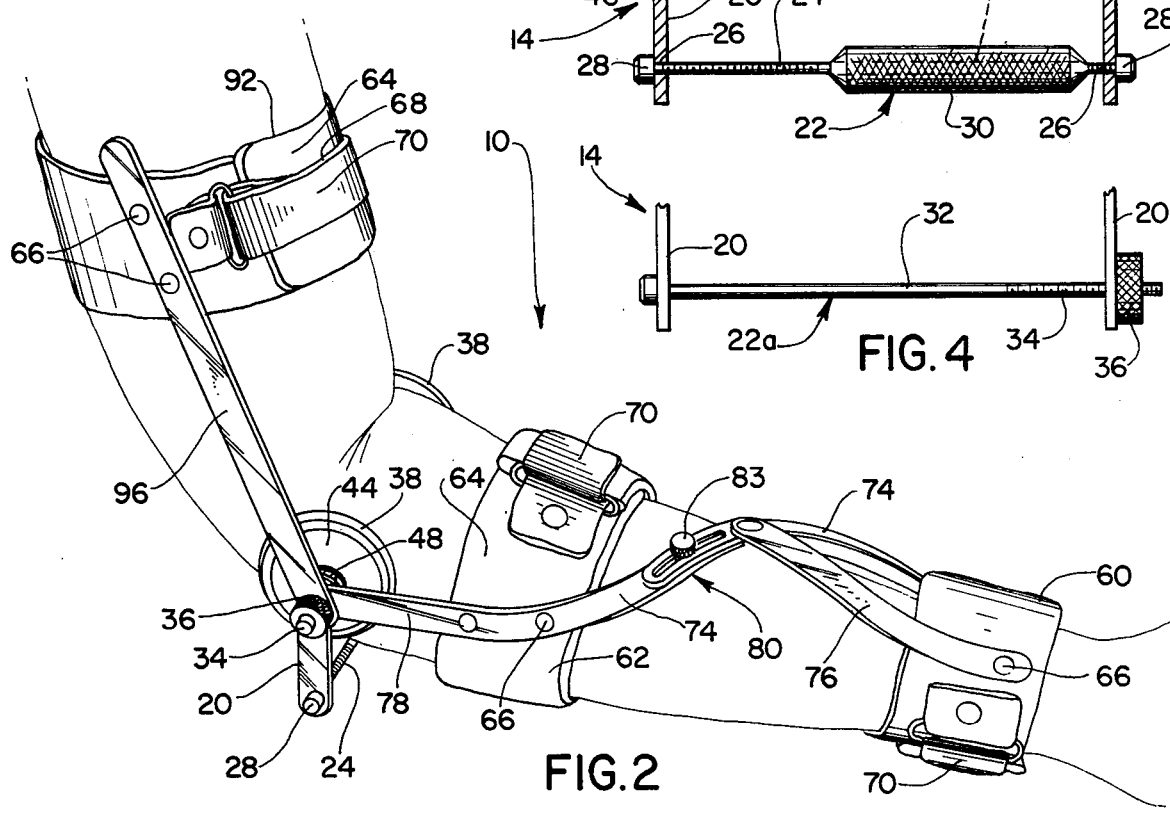

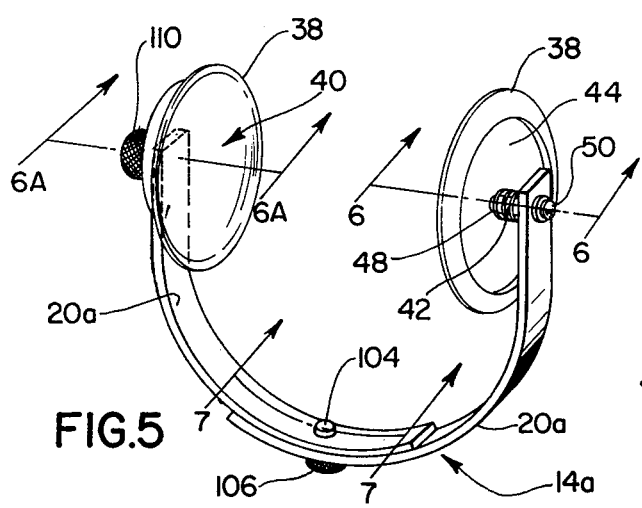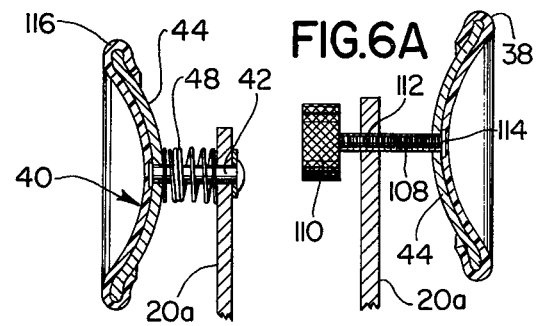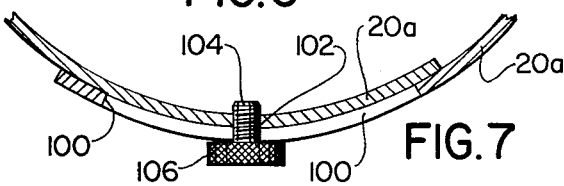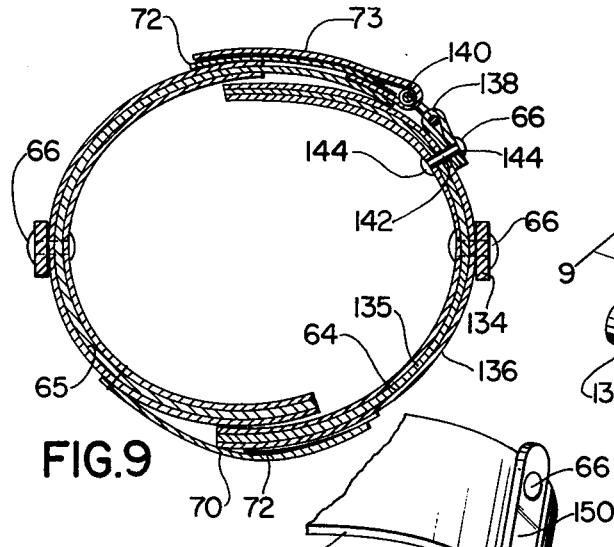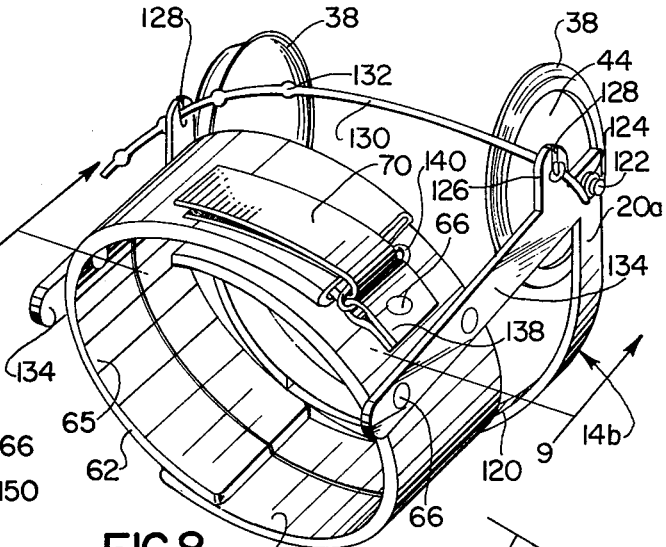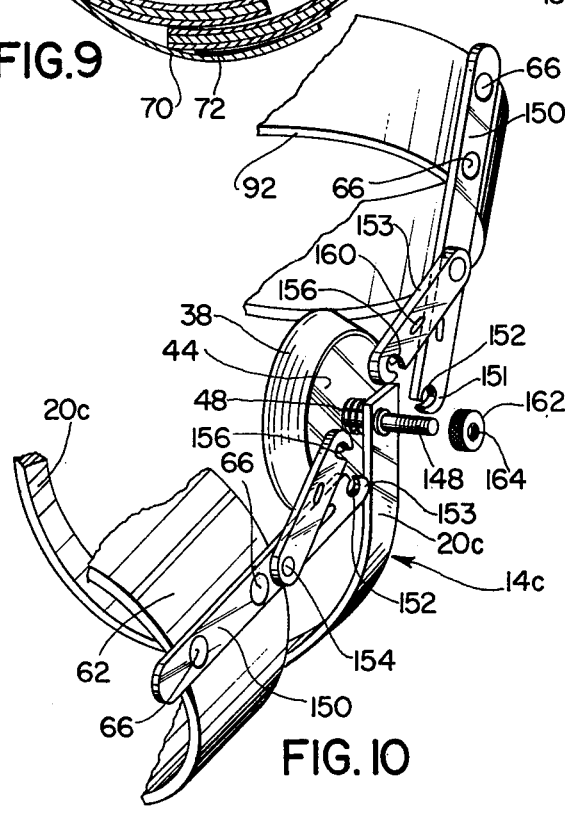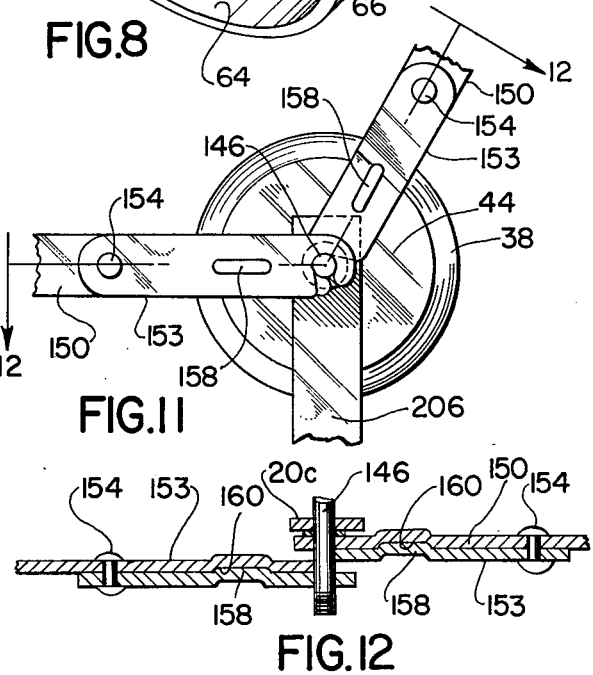

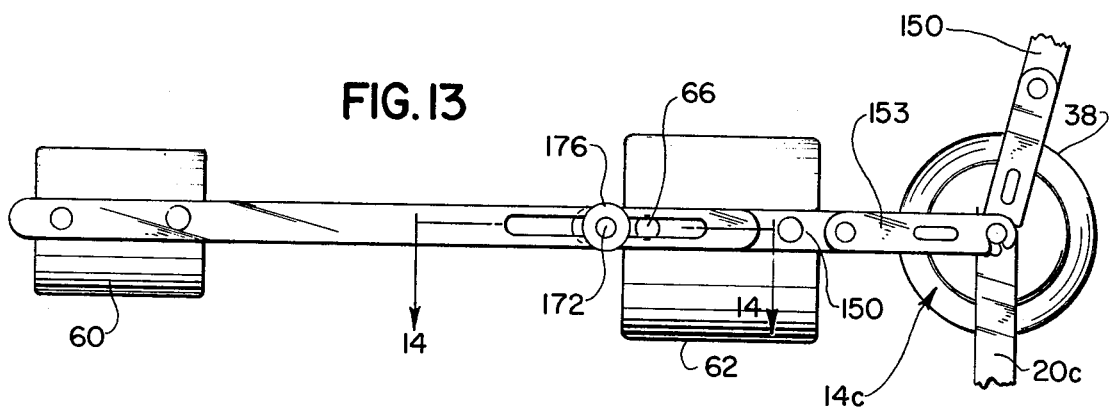
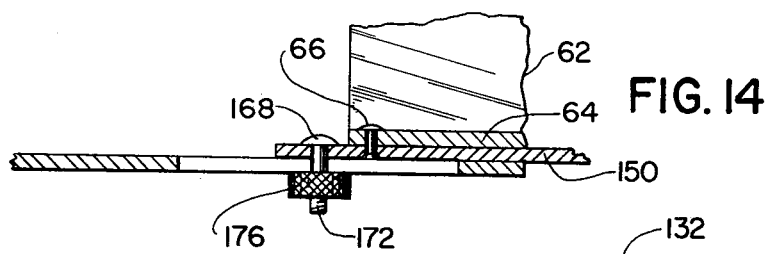
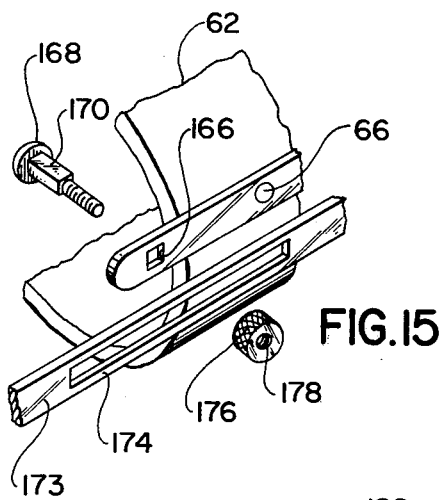
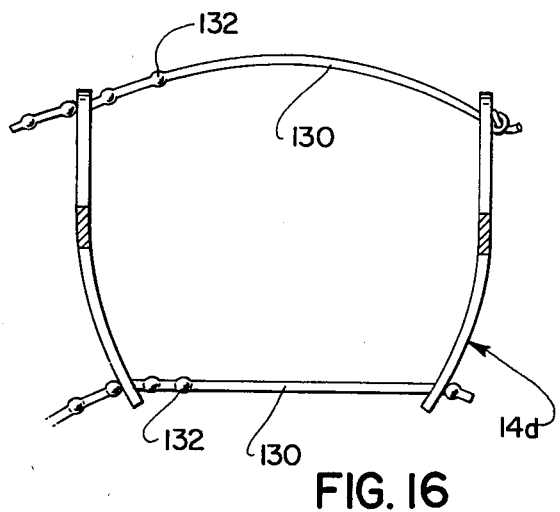
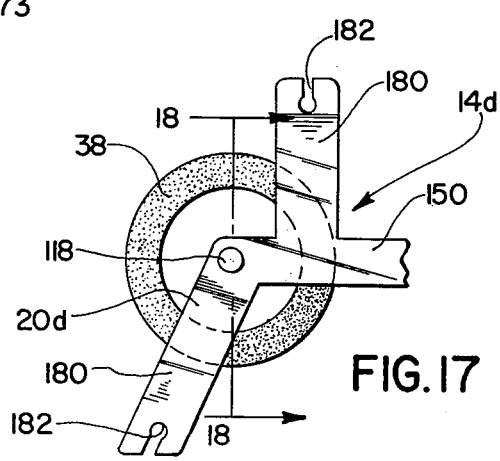
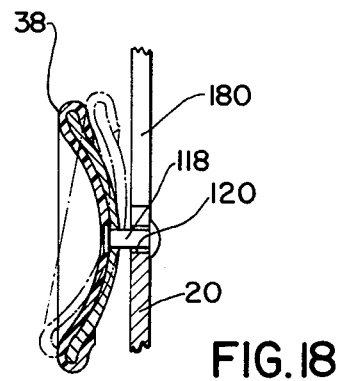

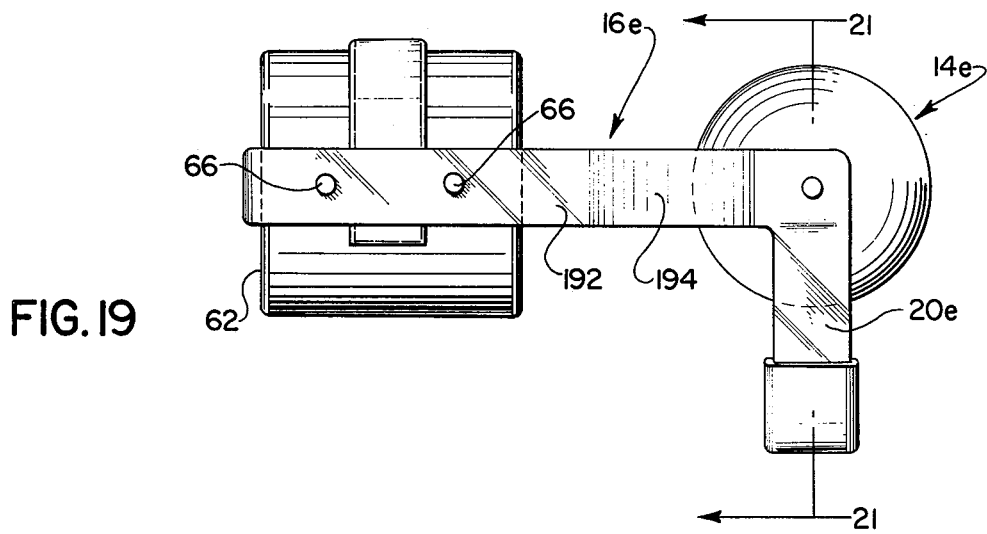
FIG.19
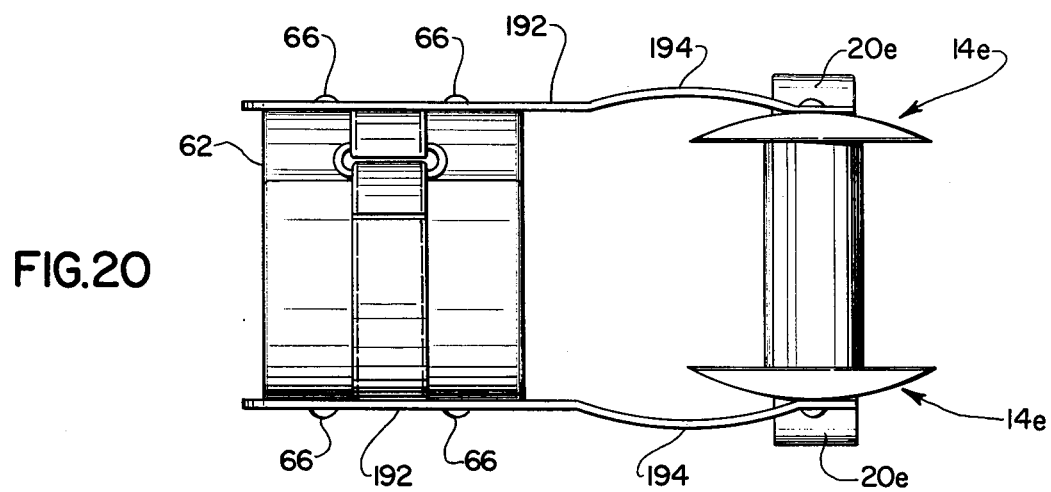
FIG.20
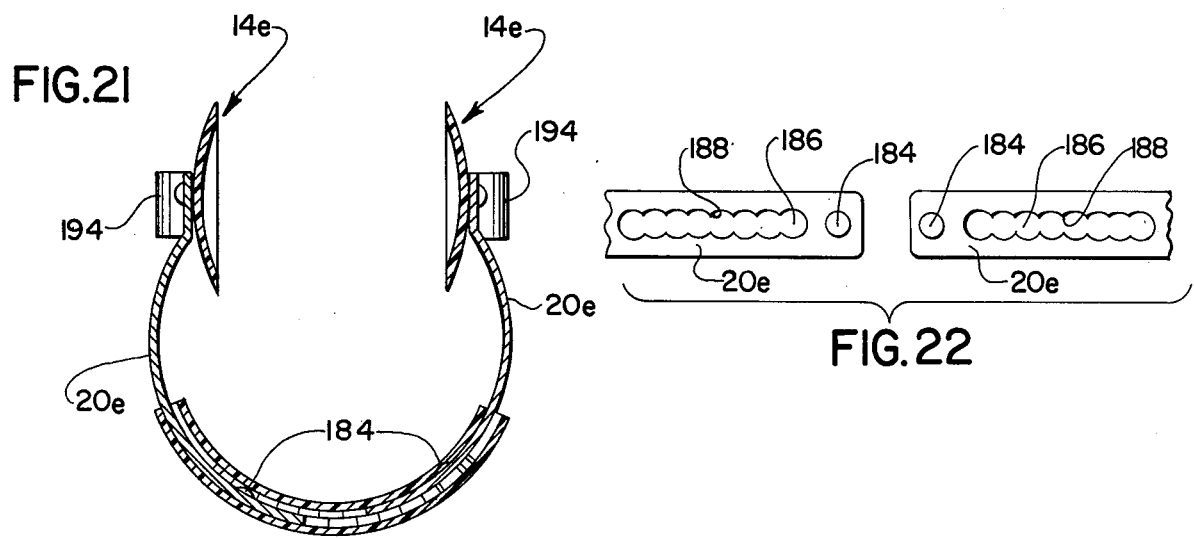
FIG.21
FIG.22

TENNIS ELBOW BRACE

BACKGROUND OF THE INVENTION

The arm or elbow injury most commonly referred to as "tennis elbow" is becoming increasingly commonplace with the recent upsurge in the popularity of tennis. Although the cause of such injury is not completely understood, it is fairly certain that the repeated impacts caused by the ball upon the racket and transmitted to the arm of the player is a basic cause of such injury. The symptoms normally include pain in the area of the elbow apparently caused by inflamation of the ligiments that serve to connect the two bones of the forearm, i.e., the radius and the ulnar, to the two spurs at the end of the humerus bone of the upper arm, that is, the medial and lateral condyles thereof. Other than rest or exercise to strengthen the arm muscles, tennis elbow is most normally treated by antiinflamatory drugs including aspirin, injection treatments of cortisone or even surgery to release the tension of the arm's tendons upon the aforementioned epicondyles. It would accordingly be desirable to eliminate or at least reduce the frequency of this injury. Also due to the persistance of players having tennis elbow to continue to play, it is particularly important that the effects thereof be minimized or prevented and it is to this end that the device of the present invention is directed.

The present inventor has accordingly determined that the effects of tennis elbow are moderated and in many cases prevented by the application of pressure to those portions of a tennis player's arm directly overlying the medial and lateral epicondyles. Such action apparently prevents or reduces the pulling action of the tendon connections with these bone spurs in such a manner that the inflamation thereof, which in turn causes the painful symptoms of tennis elbow, are reduced. Furthermore, by restricting the extremes of pronation and supination of the forearm and wrist which normally contribute to tendon extension, inflamation, and related tennis elbow symptoms are further reduced.

OBJECTS OF THE INVENTION

It is accordingly the object of the present invention to provide a device for the minimization and/or prevention of tennis elbow in which a pair of disc-like members are mounted and contact the player's arm in use in such a manner so as to apply what is believed to be a tendon-relieving pressure upon the medial and lateral epicondyles of a tennis player while engaged in such sport.

Another object of the present invention is the provision of a brace whereby such aforementioned disc-like members may be held in appropriate cooperative disposition with each other so as to enable the application of firm supporting pressure simultaneously to the medial and lateral epicondyles of the arm of a tennis player while engaged in such sport.

A still further object of the present invention is the provision of a tennis elbow brace of the type immediately aforementioned wherein such brace additionally includes means for preventing the full pronation of the wearer's forearm.

These and further objects of the present invention are accomplished by a device comprising a pair of discs adapted for respective generally nonslip compressive contact with the area of the players arm directly overlying the medial and lateral epicondyles thereof, said discs being of generally cup-shaped internal configuration and having a generally smooth somewhat compressible surface for engaging the player's skin, bracket means for mounting each of said discs in spaced opposition to each other, said bracket means permitting relatively free independent rotation of each of said discs so as to enable said discs to follow rotational movement of said epicondyles caused by normal movements of said player's arm, as during tennis play.

Other objects, features, and advantages of the invention will become apparent as the description thereof proceeds when considered in connection with the accompanying illustrative drawings.

DESCRIPTION OF THE DRAWINGS

In the drawings which illustrate the preferred embodiment presently contemplated for carrying out the present invention:

FIG. 1 is a perspective view of a full brace incorporating features of the present invention in place upon the arm of the wearer as viewed from above and proximate the medial epicondyle thereof;

FIG. 2 is a perspective view of the brace of FIG. 1 as viewed from above and proximate the lateral epicondyle thereof;

FIG. 3 is a partial sectional view taken along the line 3—3 of FIG. 1 and shows in particular one manner in which the spacing of the bracket may be modified;

FIG. 4 is a partial side sectional view similar to that shown in FIG. 3 but showing an alternate means for modifying the spacing of the bracket;

FIG. 5 is a perspective view showing the invention in its simplest form, that of a bracket having means for positioning a pair of discs to enable application of pressure to those areas of the wearer's arm immediately above the epicondyles thereof;

FIG. 6 is a partial sectional view taken along the line 6—6 of FIG. 5 and shows one manner in which pressure may be applied by one or both of the discs depicted in FIG. 5;

FIG. 6a is a side sectional view taken along the line 6a—6a of FIG. 5 and shows an alternate manner in which pressure application by one or both of the discs shown in FIG. 5 may be varied;

FIG. 7 is a side sectional view taken along the line 7—7 of FIG. 5 and shows a manner in which the spacing of the arms which in turn support the disc-like members may be varied;

FIG. 8 is a further modified form of the device from those shown in FIGS. 1 and 5 above and depicts in particular the use of a forearm brace in connection with the bracket means depicted in FIG. 5;

FIG. 9 is a sectional view taken along the line 9—9 of FIG. 8 and depicts the construction of the forearm brace in further detail;

FIG. 10 is a partial perspective view of a still further modified form of the invention wherein both forearm and upper arm braces are associated with the bracket means;

FIG. 11 is a partial side view of the modified form of the device depicted in FIG. 10 of the drawings;

FIG. 12 is a sectional view taken along the line 12—12 in FIG. 11;

FIG. 13 is a side view in somewhat stylized form depicting a still further form of the invention wherein an adjustable wrist strap or support is utilized in conjunction with the forearm strap or brace as shown in FIG. 8 of the drawings;

FIG. 14 is a partial top sectional view taken along the line 14—14 thereof;

FIG. 15 is a partial perspective view of the adjustment portion of the brace shown in FIGS. 13 and 14 and in particular shows the manner in which adjustment between the forearm and wrist support portions thereof may be effected;

FIG. 16 is an end sectional view of a still further modified form of the invention and in particular depicts an alternate manner in which spacing between the bracket means may be provided;

FIG. 17 is a partial side view as viewed from the left of the bracket shown in FIG. 16;

FIG. 18 is a partial sectional view taken along the line 18—18 of FIG. 17 and shows in particular a manner in which the disc-like element may be mounted for rocking motion;

FIG. 19 is a side elevational view of a still further modified form of the invention depicting another manner in which pressure may be applied to the condyle contacting discs;

FIG. 20 is a top plan view thereof;

FIG. 21 is an end sectional view thereof;

FIG. 22 is a partially exploded plan view of the means utilized to interconnect the bracket of that embodiment shown in FIGS. 19-21 of; drawings.

DESCRIPTION OF THE INVENTION

Figure 23:
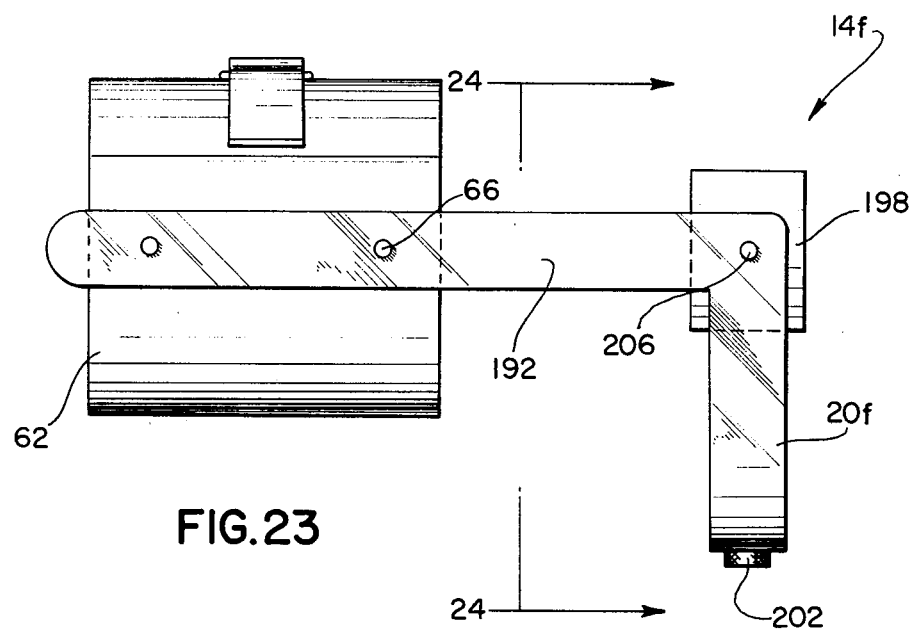
FIG. 23 is a side elevational view of a further modified form of the invention.

Turning now to the drawings and more particularly FIGS. 1 through 4 thereof, the brace 10, in its most extensive form is shown in use upon the arm 12 of a tennis player. In such form the brace 10 includes an element or disc assembly 14 adapted for positioning about the elbow areas of the wearer's arm, a forearm brace assembly 16 adapted for positioning on forearm and wrist portions of the wearer, and an upper arm brace assembly 18 adapted to be attached to the upper arm of the wearer. Both the forearm and upper arm brace assemblies 16, 18, respectively, are adapted to interconnect with the elbow brace or disc assembly 14 in a manner which will now be more fully described.

The elbow disc or bracket assembly 14 includes a pair of side arms 20 disposed in opposition to each other a distance somewhat greater than that necessary to accommodate the thickness of the wearer's elbow and adjustable from such disposition by means of adjustment means 22 which may include a pair of threaded cross bars 24 in the form of rod-like members extending through openings 26 in the lower portions of each arm 20 and affixed on opposite sides thereof by means of internally threaded nuts or members 28. The opposed ends of the threaded rods 24 are adapted to threadably engage a turnbuckle 30 which by relative adjustment thereof serves to change the spacing between the side arms 20 of the bracket assembly 14 depicted in FIG. 3.

A modified adjustment means 22a is depicted in FIG. 4 of the drawings wherein the arms 20 thereof are spaced by means of a single rod 32 threaded at one end 34 and in turn passing through and extending beyond an opening in the bottom portion thereof. The threaded end 34 of the rod 32 is maintained in place by the internally threaded knurled member 36 whereupon rotation of the member 36 permits the spacing between the arms 20 to be adjusted, as desired. In both such forms, the upper portion of each arm 20 is provided with means for mounting a pair of elements 38 which may be of disclike form in opposition to each other. Such elements are of a configuration so as to apply pressure to selected portions of the wearer's arm adjacent to or surrounding the condyles thereof as will hereinafter be more fully disclosed and preferably include a recessed or cup-like internal surface to accommodate such condyles and a peripheral surface for contacting the arm. Accordingly, the elements 38 may take the form of discs provided with an internal surface 40 which is preferably somewhat resilient, smooth, and flexible either due to the inherent formation of such disc-like members 38 from materials having such properties, e.g., rubber or plastic-like compositions, or by the covering of such discs 38 with a sleeve or the like which in turn conveys such properties to the internal surfaces 40 of such discs. Each such disc includes a rearwardly extending connecting stem or extension 42 attached in any suitable manner to the outer or rear portions 44 thereof and adapted to pass through an opening 46 provided through the top portion of each arm 20, and as depicted in FIG. 3, having a spring member 48 disposed therebetween so as to constantly urge each disc 38 towards the center of its bracket assembly 14. In the specific case of the bracket assembly depicted in FIG. 3 of the drawings, such stem or attachment means 42 takes the form of a shaft of a headed bolt 50 passing through the opening 46 and freely adapted for slidable movement with respect thereto. The shaft portion 42 of such bolt 50 may have its opposite end, however, threaded for receipt of each disc 38 in an appropriate manner so long as the terminal portions thereof do not extend beyond the internal surface 40 of the disc-like member 38, unless suitable padding is provided therein so that those portions of the arm of the wearer adapted to be received within the discs will not be subject to any discomfort caused by the end of shaft 42. It should be noted that the above mounting mechanism for the discs 38 permits not only their free, independent rotation but also causes such to be spring-urged inwardly away from the side arms 20 into close conformity with the elbow of the wearer.

When in position upon the arm of the wearer, the bracket 14 enables positioning of such discs 38 respectively over that portion of the arm immediately overlying the lateral and medial epicondyles of the wearer, such being the opposed spurs formed on the terminal end of the upper arm or humerous bone and to which the tendons which activate the forearm and other related muscles of the wearer are attached. The cup-like configuration of the inner surface 40 of the discs enable such spurs or epicondyles to be received firmly within such cup-like configuration while the peripheral edge of each disc-like member 38 causes pressure to be applied to that area surrounding such bone spurs. Such pressure applied in these areas is believed to contact portions of the tendons surrounding such spurs and attached thereto in such a manner that full extension of the tendons or their tendancy to pull away from their attachment points is minimized during the arm motions brought about, as through the playing of tennis, which in the more simple forms of the invention may be quite unrestrained, although such mobility may be reduced in the more complex forms of the invention incorporating either a forearm brace assembly 16 or an upper arm brace assembly 18, or both, as depicted in FIGS. 1 through 4 of the drawings. In any event, however, it should be clear that the discs are free to independently rotate and in this manner enable those movements which the wearer's arm are permitted to take to be smoothly followed by the discs while they are applying pressure to those areas surrounding the epicondyles of the wearer without making abrasive contact with the flesh of the wearer, as would be caused if the discs 38 were not free to rotate. It should also be pointed out that the terms condyle, epicondyle or spur each refer to the above identified bone spurs at the lower terminus of the humerous bone.

Turning again to FIGS. 1 and 2 of the drawings, the construction of the forearm brace assembly 16 is more clearly shown. Such forearm brace assembly 16 includes and is anchored by means of a wrist strap 60 and a forearm strap 62. Each such strap preferably includes a band or web portion 64 adapted to encircle that portion of the arm with which it is in contact and through which fasteners 66 project. Such fasteners either may be permanently affixed to a support such as the straps 60 and 62 depicted or may be separable therefrom as suits the particular installation and specifically serve as the means by which brace members are anchored to particular locations thereon. The brace members serve to interconnect the straps 60 and 62 to each other and to the bracket assembly 14. It should also be apparent that such straps 60 and 62 are provided with adjustment means 68 which may be in the form of an overlapping substrap 70 connected to the main strap portion 64 at one side and adapted by means of Velcro type fastening means to be connected to an underlying pad 72 of such material.

A first brace member 74 of generally curved configuration having a bifurcated end member 76 and a single end 78 is fixed at the single end 78 thereof to the lateral or outer side of the bracket assembly 14, as by the provision of an opening therethrough, through which the stem or shaft portion 42 of the bolt 50 may pass and accordingly serves to anchor such end 78 of the first brace member 74 in position. This first brace member 74 is adapted to curve over the forearm of the wearer and extend to the lower end of the ulnar bone at the styloid process thereof, that is, the wrist strap or other anchor means 60 includes a fastener 66 positioned to overlie that portion of the wearer's wrist at the lower end of the ulnar at the styloid process and to which the opposite end of the first brace member 74 is adapted to be connected as depicted. Such first brace member 74 may be of two-piece construction and interconnected by adjustable connection means 80 so that opposed portions of the brace 74 are adapted to slide in overlying contact with each other. A slot 82 may be provided in that portion of the brace 74 disposed uppermost and an aligned threaded opening in the underlying portion so that the knurled nut 83 having a downwardly extending threaded shaft (not shown) is adapted to fix the relative length of such brace and accordingly adjust same for different size wearer arms.

The bifurcated end 76 of such first brace member 74 originates, that is, is connected to that portion of the wrist strap 60 overlying the top of wrist as through connection means 66 (note FIG. 2) and passing therefrom to a point approximately two-thirds of the way of the back of the forearm and attached at that point to the curved portion of the brace member 74. Such connection between the brace members 76 and 74 occurs below that point at which the adjustable means 80 is provided.

The second major brace 84 is also preferably of two-piece construction and includes an upper brace member 86 and a lower brace member 88. The upper brace member 86 is connected at one end to the bracket assembly 14 (adjacent the medial condyle) in any suitable manner including that above described in relationship to the connection of the first brace 74 to the bracket assembly 14, thence anchored in position by the forearm strap 64 by means of fastening means 66 and thence to a terminal portion having an adjustable mechanism 90 similar to that above described in regard to brace member 74. The lower brace member 88 is connected by such adjustable mechanism 90 to the upper brace member 86 and is slidable therewith to enable the overall length of brace 84 to be adjusted. The opposite end of the lower brace member 86 is anchored to wrist strap 60.

The above described bracket assembly 14 and forearm brace assembly 16 interact so as to prevent the extremes of pronation and supination of the forearm and wrist which are throught to contribute to tennis elbow. Thus accordingly not only are the arm movements which are believed to contribute to tennis elbow minimized but at the same time by reason of the pressure application at the condyles, those tendon muvements, contractions, or extensions which are permitted are controlled so that their effect at the attachment points with the lateral and medial condyles is also minimized.

As previously indicated the brace construction depicted in FIGS. 1 through 4 of the drawings includes an upper brace assembly 18 in addition to the bracket assembly 14 and the forearm brace assembly 16. Such upper brace assembly 18 includes an upper arm strap 92 forming an anchor, that is, locating the brace assembly on and with respect to the upper arm. Such strap 92 may include, as with previous straps, a web portion 64 and fastening or adjustment means 68 whereby the tightness of the encircling web 64 about the upper arm may be adjusted, including a strap 70 overlying a pad 72 both of which are provided with Velcro type attachment means so as to facilitate easy attachment and removal. Both sides of the upper brace assembly 18 are provided with brace members 94 and 96 respectively attached, as by attachment means 66 to opposite sides of the strap 92 and extending for connection to the lateral and medial arm portions of the bracket assembly 14. Specifically, as with the previously discussed brace members 74 and 84, the brace members 94, 96 are attached to the upper portions of the bracket assembly arms 20, as by the provision of openings 98 therein, through which the connection means for the opposed discs 38 is adapted to pass. In this manner then, when it is desired to detach either or both of the brace assemblies 16, 18 from the bracket assembly 14, the disc attachment means may be temporarily removed from one or both of the arms 20, the appropriate brace member removed and the disc attachment means reassembled.

When positioned and adjusted on the arm of a wearer, the full brace 10 as above described and including not only the elbow or bracket assembly 14 but both the forearm brace assembly 16 and the upper brace assembly 18, is able to materially modify the extent of movement of the wearer's arm so as to prevent both the extremes of pronation and supination of the forearm and wrist. The brace is also useful to keep the arm straight, especially on the backhand stroke. Furthermore, while restricting the arm from the twisting motions believed to cause extension of the forearm tendons and accordingly inflamation of those tendon attachment points with the condyles, the brace 10 does not restrict the pivotal movement of the wearer's forearm in relationship to the upper arm inasmuch as forearm brace assembly 16 and the upper arm brace assembly 18 are both free to pivot independently of each other about their connection with the bracket assembly 14. At the same time the above indicated control is imparted to the wearers arm, the discs 38 constantly apply a firm supporting pressure about those areas surrounding and overlying the condyles in the aforementioned manner described. This action is believed to control the amount of tendon tension at such attachment points and thus relieve, reduce, or eliminate the inflamation and tendon pain associated therewith. It should be brought out, however, that it is not always necessary to utilize the full brace configuration depicted in FIGS. 1 through 4 of the drawings and accordingly, it should be clear that dependent upon the type restriction desired to place upon the arm, that either or both of the brace assembly 16, 18 may not be utilized.

Thus, as depicted in FIGS. 5 through 7, a modified bracket assembly 14a is depicted wherein neither forearm or upper arm brace assemblies are utilized therewith. In such modified construction, a pair of brace arms 20a each of inwardly curved configuration are interconnected at their lower terminal ends by means of a slot 100 located in one of such arms 20a and a threaded opening 102 located in the other thereof. A threaded shaft 104 having a head 106 larger than the width extension of the slot 100 is adapted to pass through the slot 100 into engagement with the threaded opening 102 and in that manner serves to form the adjustment means by which the lateral spacing of the upper ends of the arms 20a may be varied with respect to each other. Inasmuch as the modified bracket assembly 14a cannot rely upon attachment to associated brace means for positioning upon the wearer's arm, the opposed discs 38 supported thereby must firmly engage the wearer's arm above the condyle areas thereof so as not to become displaced partially or entirely during use. Accordingly, as shown in FIG. 6a of the drawings, means for adjusting the relative positioning of one of the discs 38 is provided in the form of a threaded shaft 108 having an enlarged head 110 which may be knurled to assist in the positioning of such shaft within a threaded opening 112 provided within the upper portion of one of the bracket arms 20a. The other end of the shaft 108 is provided with a disc 114 or other means by which it may pass through the outer surface of the disc 38 and be held against the inner surface 40 thereof. Instead of an enlarged disc 114, the shaft 108 may be permanently attached as by known mechanisms, i.e., welding, brazing, etc., as well as by temporary attachment means, i.e., a threaded disc (not shown). In this manner then, the effective distance between the two discs may be regulated so as to assure a firm supporting engagement of the inner surfaces 40 thereof with the opposed condyles of the wearer, it being clear that minor differences in the extent thereof, brought about by movement of the arm, as during tennis play, will be accommodated by the biasing action of spring 48 on the remaining disc 38, as illustrated by the supporting structure previously described in relationship to FIG. 3. By way of review, such includes a shaft 42 passing through an opening in the upper portion of the arm 20a and constantly inwardly urged by means of the action of spring 48 interengaged between the arm 20a and the outer surface 44 of the disc 38. Accordingly, while such mechanism constantly urges the opposed disc 38 into opposition with the other disc, it also permits an outward flexure or movement of such disc, as through the compression of spring 48, it being clear that rod 42 is free to move outwardly or to the right, as shown in FIG. 6 of the drawings.

As best shown in FIGS. 6 and 6a, each of the discs 38 may alternatively be formed of metal and provided with a sleeve 116 preferably of a soft compressible covering such as known fabrics or rubberized material layers, rather than the formation of each disc directly from a rubber-like or plastic material, although the latter is preferred. In either event, the necessary protective flesh contacting surface for contact with the wearer is provided. Also it should be clear that as previously indicated each of the discs 38 is free to independently rotate about its mounting shaft 42 or 108, as the case may be, thereby reducing any restrictive action by the discs 38 against pivoting movement of the forearm about the elbow joint.

Also, and as specifically illustrated in FIG. 18 of the drawings, in some cases it is desirable that in addition to providing such independent rotational movement generally in a plane paralleling the upper portion of one or both of the arms 20a, that a revolving, swiveling, or rocking type motion out of such plane may be additionally provided so as to better enable the discs to follow more complex movement of the condyles during tennis play. Such action may be facilitated by the use of a nonthreaded bolt 118 passing through an opening 120 within one of the arms 20 in such a manner so as to provide considerable vertical play therebetween so as to in turn permit movement of the disc 38 from the position depicted in the solid line illustration to that depicted in the phantom-line representation. It should be clear, however, that such additional rocking type motion may be utilized with any of the forms of the invention depicted in the various drawing figures.

Turning now to FIG. 8 of the drawings, a further embodiment of the brace 10 of the present invention is depicted wherein the discs 38 thereof are held in spaced position by means of a one-piece elbow loop of generally U-shaped configuration and the gross adjustment therebetween inherently provided in various size models or alternatively provided with adjustment mechanism such as that shown in FIG. 7 of the drawings. In this brace configuration, however, each of the discs 38 is mounted in a nonresilient fashion to the bracket assembly 14b, that is, they are directly affixed thereto as by means of an outwardly projecting threaded shaft 122 having retaining means such as a nut 124 attached thereto. In order to provide a measure of adjustment in the spacing between the opposed discs 38 in such 14b bracket assembly form of the brace 10, the upper end of each opposed arm 20b is provided with a boss 126 upwardly extending and provided with an upwardly opening slot 128 in which a flexible cord 130 having a series of enlargements or knots 132 is adapted to be positioned. The flexible cord or rod 130 may be formed of various materials which may include elastic material so that a finer adjustment to the pressure applied to the condyles by the opposed discs 38 may be obtained or may be adjusted preliminary to various modes of play, that is, a tighter relationship might be desired if one were practicing slams or other tennis movements that would involve a greater degree of elbow movement. In such form of the bracket assembly 14b, a forearm strap 62 may be additionally utilized and positioned thereon by means of opposed bracket members 134 attached as previously discussed by means of connection means 66. The particular construction that such forearm strap 62 may take, as well as the other straps discussed in the present invention, is best understood by simultaneous reference to FIGS. 8 and 9 of the drawings wherein a first strap segment 64 preferably formed of an appropriate textile material including an inner core 135 and an outer fabric surface 136 such as to assure frictional or nonslip contact with the skin of the wearer is provided. A second strap segment 65 of similar construction is adapted to overlie a portion of the first segment 64 at the top thereof and underlie such segment at the bottom portion thereof. Each of the segments 64, 65 is provided at one terminal end thereof with an outer pad 72 of Velcro type material adapted for interconnecting contact with an overlying strap 70, as previously indicated. Such strap 70 may be integrally connected to the segments 64, 65 as specifically shown in the case with segments 65 in FIG. 9 of the drawings, or may take the form of a tongue 73 extending forwardly of the terminal portion of such segment at the end having the Velcro attachment pad 72, for positioning through a buckle 138 having a keeper portion 140, as specifically shown in connection with segment 64 in FIG. 9 of the drawings. Such buckle is adapted to be held or positioned by means of fastening means 66, the details of which may include a rivet 142 adapted to pass through the full extent of one such segment 64 or 65 and provided with opposed enlarged heads 144 on either side thereof. The fastening means 66 utilized to interconnect the brace assembly 14b, as shown in FIG. 8, with the brace members 134 shown therein and all other respective strap/brace member attachments throughout the description hereof may be by means of such configuration attachment means 66 as above described.

Turning now to FIGS. 10 through 12 of the drawings, a modified form or manner in which the forearm and/or upper arm braces or portions thereof may be attached to the bracket assembly 14 of the present invention is depicted, such modified bracket assembly being referred to as 14c in this instance. In such case, the upper arms 20c of the bracket assembly 14c is provided with an opening through which a shaft 146, which may extend from each disc 38 or which may be a separate shaft (not shown), projecting outwardly therethrough and being provided at its outward terminal end with a threaded portion 148; the remainder of the shaft 146 having a smooth surface. In such embodiment, modified brace members 150 are connected at one end thereof to the forearm and upper arm braces 62, 92 respectively, and provided at the other ends thereof with a terminal portion 151 having hook-shaped opening 152 adapted to receive a portion of the shaft 146. A second or keeper element 153 is pivotally positioned about a connector 154 to a portion of that brace member 150 somewhat removed from the terminal end 151 thereof. Each such keeper 153 is provided with a hook-shaped opening 156 similar in configuration to opening 152 but opening in a downward direction and in turn adapted to receive a portion of the shaft 146 and in this manner provide the mechanism by which brace members 150 may be quickly removed from attachment to the bracket assembly 14c without disturbing a remaining brace member 150, as in those cases when it is desirable to initially position both a forearm and upper arm brace assembly and thereafter remove one or the other thereof. In order to assure that the keeper elements 153 do not have excessive lateral movement, a detent 158 (FIG. 12) is provided on the outer side of each of the members 150 to mate with a dimple or opening 160 provided in each keeper element 153 so as to cooperatively engage therewith. Such provision also affords the means by which the keeper elements 153 may be prevented from freely pivoting about a pivotal connection 154 when not in use. A knurled nut 162 having a threaded internal bore 164 for engagement with the threaded end 148 of shaft 146 is utilized to maintain the brace members 150 as above described in position on the bracket assembly 14c.

Additionally and as best shown in FIGS. 13 through 15 of the drawings, the brace 10 of the present invention may be utilized either with a forearm strap 62 solely, as shown in FIGS. 8 through 12, or in conjunction with an additional anchor provided by a wrist strap 60 similar to that depicted in FIGS. 1 through 4 of the drawings. In this embodiment, and as shown in FIGS. 13 through 15, the brace member 150 may be provided at its terminal end distal from the bracket assembly 14 with an opening, i.e., the square-shaped opening 166, for receipt of a bolt 168 having a square shank 170 from which a threaded shaft 172 of reduced diameter outwardly projects. The shank 170 is adapted to be nonrotatably received within the opening 166 and the shaft 172 projects outwardly through an elongated slot 174. A knurled nut 176 having an internally threaded bore 178 is adapted to threadably connect with the shaft 172 in such a manner as to permit adjustment of the effective length of member 150 whereby the distance between bracket means 14c and wrist strap 60 may be adjusted to accommodate different length arms.

Alternatively, as shown in FIGS. 16 and 17, a bracket assembly 14d having opposed arms 20d each provided at opposite sides thereof with extending portions 180 similar to elements 126 depicted in FIG. 8 may be provided. Each such portion 180 is provided with a terminal key-shaped slot 182 in which flexible cords 130 having spaced knotted or enlarged portions 132 are provided and in this manner the side arms 20d making up the bracket assembly 14d are not only supported upon the wearer's arm, but also the relative tightness of such support may be readily adjusted so as to effect proper pressure of the discs 38 on the condyles of the wearer. Naturally, the bracket assembly 14d could be mounted upon the arm of the wearer either by initially loosely affixing each connector cord 130 to the arms 20d thereof or one at a time as the case may be, but in either event, a particularly simple and inexpensive construction is afforded for mounting the bracket assembly with the attached discs 38 to accomplish the objectives of the invention.

Turning now to FIGS. 19-22 of the drawings, a still further form of the invention including an alternate bracket assembly 14e is depicted. Such bracket assembly 14e includes a pair of opposed arms 20e connected together underneath the elbow at one end and each provided with a disc 38 at the other end. The arms are preferably formed of spring steel and are outwardly bowed or of other suitable configuration so as to form a leaf spring action to continually urge the discs 38 into contact with areas of the person adjacent his or her condyles. In order to accommodate different size elbows the connected portions of the arms 20e may be slidably moved with respect to each other. Such variable connection may be accomplished by providing each terminal end thereof with a bulbous member 184 and a series of openings 186 interconnected to each other by reduced width slots 188. The relative disposition of the bulbous member and the slotted openings of each arm 20e is such that the member is disposed generally in line with the opening but more proximal to the adjacent terminal end thereof. The bulbous members 184 are preferably either both upwardly or downwardly orientated and accordingly the member of one of the arms 20e is adapted to interfit with a superimposed opening 186 in the other of the arms 20e when the two arms are disposed in at least partial overlying relationship. The bulbous members 184 also are preferably of a width so as to pass through slots 188 so that once interconnected, the arms 20e can be slid relative to each other so as to adjust the pressure exerted by the discs 38. Such slidable adjustment, as above described, serves to achieve a general or rough adjustment of the bracket assembly 14e to the wearer's elbow while the inherent spring action of the arms 20e serves to place a continual pressure on the condyles via discs 38. The discs may be attached to the arms 20e in any of the manners above discussed with regard to the other embodiments of the invention although since the spring action for urging such into contact with the areas adjacent the wearers is inherently provided by the above described leaf spring action, the inclusion of separate spring members as shown in several previously disclosed embodiments could be omitted. However, retention of a freely swivable action would be desirable and such is provided by the inclusion of the pivot pin 190 shown.

In addition, the bracket assembly 14e may include forearm brace assembly 16e including a pair of spaced brace members 192 each attached at one end thereof to a forearm strap 62, as by fasteners 66, so as to more positively anchor the bracket assembly 14e in position, and at the other end thereof to the arm 20e by any suitable means. Alternatively, the arm 20e may integrally include brace member 192. In either case, each of the brace members 192 are of spring steel or other material which will inherently tend to return to shape after distortion and are spaced so they are so distorted when the bracket assembly 14e is positioned on the wearer. In this way, then, continual pressure is brought to bear on the wearer's condyles via the discs 38. The brace members 192 preferably include outwardly bowed or bulged portions 194 to concentrate inward spring pressure at their points of connection with the discs 38. In order to protect the wearer from possible rough surfaces on arms 20e, a sleeve 196 of plastic or other preferably transparent and cushioning material is disposed over the interconnected ends thereof. It should also be brought out that in this embodiment, and in the others above described, that the discs 38 may be in the form of rubber or soft plastic suction cups having inner peripheral surfaces adapted for contact with those areas surrounding the wearer's condyles and a central interior surface of greater extent than that needed to accommodate the wearer's condyles and accordingly present the opportunity for being held by suction in contact with the wearer's skin immediately surrounding his or her condyles.

Figure 24:
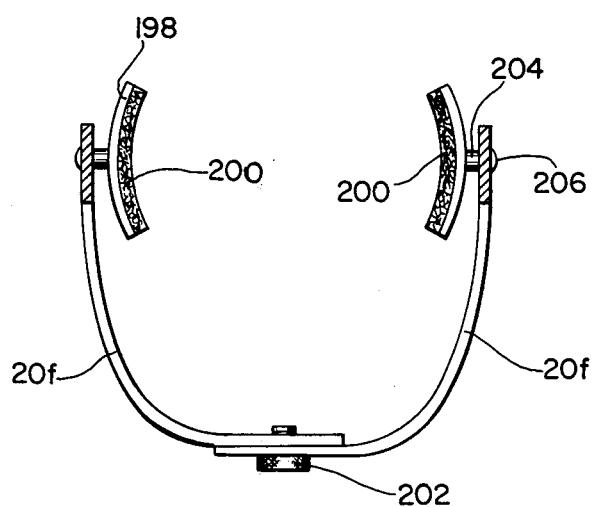
FIG. 24 is an end sectional view thereof taken along the line 24—24 of FIG. 23.

Turning now to FIGS. 23 and 24 of the drawings, another from of the invention is shown. Such form is similar to that shown in FIGS. 19-22 except that a modified bracket assembly 14f is disclosed and that the adjusting mechanism of such bracket assembly is similar to that shown in FIGS. 5-7. Thus the bracket assembly 14f includes a pair of opposed arms 20f connected together underneath the elbow at one end as by adjusting means 100-106 and provided with an element 198 of modified configuration from disc 38. Such element may be of generally rectangular arcuate form having an inwardly directed face portion adapted to receive a pad 200 of fibrous cushioning material to accommodate the condyles of a wearer while simultaneously permitting pressure to be placed on areas adjacent thereto. While in this form of the invention pressure application does not surround the condyles, the element is rotatably adjustable about its connection with the arms 20f to enable placement thereof at different arcuate dispositions and thus permit pressure to be applied at opposed locations adjacent the condyles. Furthermore, the element 198 may be other than rectangular, i.e., include several lobes, and in this fashion permit pressure application at several spaced locations in those applications where such is adequate or desirable to alleviate "tennis elbow" symptoms. The connection of element 198 to the opposed arms 20f may be accomplished by any of the means 202 similar to means previously disclosed, i.e., those specifically indicated in FIGS. 3, 6, 6A and 18, to permit rotational movement of the element or disc 198 to conform to the expected tennis arm movements or may, when of a configuration adapted to apply pressure at specific spaced locations, such as the rectangular format shown, be dampened to reduce the free rotational movement with respect to arms 20f thereof and accordingly increase the assurance of adjustably being able to apply such force in specific predetermined areas. Such dampening may be accomplished by the mounting of the elements 198 to the arms 20f by means of a threaded bolt passing internally through a spacer, such bolt having a head 206 and an adjusting nut (not shown) covered by pad 200 so as to regulate the resultant pressure application between outer element surfaces and the spacer to in turn accomplish an adjustability in the freedom of relative rotational movement therebetween.

From the foregoing descriptions, it is believed that a most desirable device in several constructional formats has been disclosed which effectively accomplishes the several objects of the invention and that such modes are readily formable from available materials with known techniques. It should be pointed out, however, that various other fabrication modes and constructional formats may be possible and that it is intended that such should be included in the present invention to the extent covered in the following claims. Specifically, in that regard, the term disc is utilized therein in a broadly generic sense to include elements of a general disc-like nature other than circular plates such as elliptical, rectangular and irregularly shaped generally planar elements so constructed to enable application of pressure to areas adjacent the wearer's condyles.

What is claimed is:

1. A device adapted for wear by a tennis player for minimizing and/or preventing tennis elbow comprising, a pair of elements adapted for respective generally compressive contact with the area of said player's arm adjacent the medial and lateral condyles thereof, bracket means for mounting each of said elements in spaced opposition to each other, said bracket means permitting the adjustment of each of said elements so as to enable said elements to apply pressure to specific areas of said player's arm so as to relieve at least some of the tension applied to said condyles normally caused by the movements of said player's arm during tennis play, said device including forearm brce means extending from opposite sides of said bracket to anchor means adapted for connection to the forearm of the wearer, said anchor means including at least an upper foremarm strap adapted for positioning proximal the wearer's elbow, said forearm brace means including separate first and second relatively stiff brace members connected respectively to the lateral and medial sides of said bracket and to generally opposite sides of said forearm strap, and including spring means for continually urging said elements against said condyle adjacent arm areas.

2. The device of claim 1, said elements being discs of generally cup-shaped internal configuration.

3. The device of claim 1, said forearm strap being adjustable to accommodate varying sized forearm dimensions.

4. The device of claim 1, said elements having a generally circular peripheral portion respectively directly overlying said medial and lateral condyles.

5. The device of claim 1, said bracket means permitting relatively free independent rotation of each of said elements so as to enable said elements to follow rotational movement of said condyles caused by normal movements of said player's arm as during tennis play.

6. A device adapted for wear by a tennis player for minimizing and/or preventing tennsi elbow comprising, a pair of elements adapted for respective generally compressive contact with the area of said player's arm adjacent the medial and lateral condyles thereof, bracket means for mounting each of said elements in spaced opposition to each other, said bracket means permitting the adjustment of each of said elements so as to enable said elements to apply pressure to specific areas of said player's arm so as to relieve at least some of the tension applied to said condyles normally caused by the movements of said player's arm during tennis play, said device including forearm brace means extending from opposite sides of said bracket to anchor means adapted for connection to the forearm of the wearer, said anchor means including at least an upper forearm strap adapted for positioning proximal the wearer's elbow, said forearm brace means including separate first and second relatively stiff brace members connected respectively to the lateral and medial sides of said bracket and to generally opposite sides of said forearm strap, said bracket means having a pair of arms, said arms supporting said elements at first ends thereof and interconnected at second ends thereof by means for adjusting the relative positioning of said bracket arm second ends with respect to each other so as to modify the spacing of said elements.

7. The device of claim 6, said arms cooperatively forming a U-shaped bracket adapted for positioning beneath the wearer's elbow, each of said arms having second end terminal portion adapted for adjustable slidable contact with each other and means for maintaining said second ends in a fixed relative position.

8. The device of claim 7, one of said bracket arms first ends having means for independently adjusting the spacing of at least one of said elements.

9. The device of claim 8, the other of said bracket arms first ends having independent spring means for continually urging said elements against said condyles.

10. A device adapted for wear by a tennis player for minimizing and/ or preventing tennis elbow comprising, a pair of elements adapted for respective generally compressive contact with the area of said player's arm adjacent the medial and lateral condyles thereof, bracket means for mounting each of said elements in spaced opposition to each other, said bracket means permitting the adjustment of each of said elements so as to enable said elements to apply pressure to specific areas of said player's arm so as to relieve at least some of the tension applied to said condyles normally caused by the movement of said player's arm during tennis play, said device including forearm brace means extending from opposite sides of said bracket to anchor means adapted for connection to the forearm of the wearer, said anchor means including at least an upper forearm strap adapted for positioning proximal the wearer's elbow, said forearm brace means including separate first and second relatively stiff brace members connected respectively to the lateral and medial sides of said bracket and to generally opposite sides of said forearm strap, said bracket means having a pair of arms, said arms supporting said elements at first ends thereof and interconnected at second ends thereof by means for adjusting the relative positioning of said bracket arm second ends with respect to each other so as to modify the spacing of siad elements, said arms cooperatively forming a U-shaped bracket adapted for positioning beneath the wearer's elbow, each of said arms having second end terminal portion adapted for adjustable slidable contact with each other and means for maintaining said second ends in a fixed relative position, one of said bracket arms first ends having means for independently adjusting the spacing of at least one of said elements so as to assure maintenance of pressure upon said specific player arm areas.

11. The device of claim 10, said means for maintaining said second ends in a fixed relative position including an axially orientated slot in the outer of said second end terminal portions and a threaded opening disposed adjacent said slot in the other of said second end terminal portions and a threaded bolt having an enlarged knurled head adapted to pass through said slot and threadable engaged with said opening so as to fix the position of each of said arms relative to each other.

12. A device adapted for wear by a tennis player for minimizing and/or perventing tennis elbow comprising, a pair of elements adapted for respective generally compressive contact with the area of said player's arm adjacent the medial and lateral condyles thereof, bracket means terminating in laterally spaced free ends and positioned generally beneath the wearer's elbow with said free ends thereof proximal said condyles when said device is properly worn by a person, said elements respectively mounted on said bracket means proximal said free ends in spaced opposition to each other, said bracket means permitting the adjustment of each of said elements so as to enable said elements to apply pressure to specific areas of said player's arm so as to relieve at least some of the tension applied to said condyles normally caused by the movements of said player's arm during tennis play, said device including forearm brace means extending forwardly from opposite sides of said bracket to anchor means adapted for connection to the forearm of the wearer, said anchor means including at least an upper forearm strap adapted for positioning proximal the wearer's elbow, said forearm brace means including separate first and second relatively stiff brace members connected respectively to the lateral and medial sides of said bracket and to generally opposite sides of said forearm strap.

13. The device of claim 12, said elements having a generally circular peripheral portion respectively directly overlying said medial and lateral condyles.

14. The device of claim 12, said bracket means permitting relatively free independent rotation of each of said elements so as to enable said elements to follow rotational movement of said condyles caused by normal movements of said player's arm as during tennis play.

* * * * *